(12) United States Patent
Krebs (10) Patent No.: US 11,801,489 B2
(45) Date of Patent: Oct. 31, 2023

(54) MEDIA FOR SEPARATING SMALL MOLECULES FROM BIOMACROMOLECULES IN AQUEOUS MIXTURES

(71) Applicant: Joseph F. Krebs, Austin, TX (US)

(72) Inventor: Joseph F. Krebs, Austin, TX (US)

( * ) Notice: Subject to any disclaimer, the term of this patent is extended or adjusted under 35 U.S.C. 154(b) by 229 days.

(21) Appl. No.: 17/215,110

(22) Filed: Mar. 29, 2021

(65) Prior Publication Data
US 2022/0305461 A1  Sep. 29, 2022

(51) Int. Cl.
| | |
|---|---|
| *B01J 20/29* | (2006.01) |
| *B01J 20/291* | (2006.01) |
| *B01J 20/24* | (2006.01) |
| *B01J 20/26* | (2006.01) |
| *B01J 20/28* | (2006.01) |
| *C07K 1/16* | (2006.01) |
| *B01D 15/34* | (2006.01) |

(52) U.S. Cl.
CPC ............ *B01J 20/291* (2013.01); *B01D 15/34* (2013.01); *B01J 20/24* (2013.01); *B01J 20/261* (2013.01); *B01J 20/262* (2013.01); *B01J 20/28016* (2013.01); *B01J 20/28047* (2013.01); *B01J 20/28052* (2013.01); *C07K 1/16* (2013.01); *B01J 2220/52* (2013.01)

(58) Field of Classification Search
CPC ........ B01J 20/291; B01J 20/24; B01J 20/261; B01J 20/262; B01J 20/28016; B01J 20/28047; B01J 20/28052; B01J 2220/52; B01D 15/34; C07K 1/16
See application file for complete search history.

(56) References Cited

U.S. PATENT DOCUMENTS 10,864,512 B2 * 12/2020 Maloisel .............. B01J 20/3285

* cited by examiner

*Primary Examiner* — Taiwo Oladapo
(74) *Attorney, Agent, or Firm* — Lewellyn Law, PLLC; Stephen Lewellyn (57) ABSTRACT

A separation medium for removing small molecules from biomacromolecule in aqueous mixtures comprises gel filtration chromatography beads having a nominal protein fractional range of about 1000 Da to about 5000 Da and having an internal adsorbent matrix derived from a hydrophobicized scaffold. The gel filtration chromatography beads remove small molecules that are less than 1500 Da and have log Pow values greater than about −0.5 from biomacromolecules in aqueous mixtures. Devices containing the separation medium are also provided.

21 Claims, 2 Drawing Sheets

MEDIA FOR SEPARATING SMALL MOLECULES FROM BIOMACROMOLECULES IN AQUEOUS MIXTURES

FIELD OF THE INVENTION

Embodiments of the invention relate to the field of protein conjugation reactions and, more particularly, to systems and media for separating small molecules from biomacromolecules in aqueous mixtures, such as aqueous protein conjugation reaction mixtures, for example.

BACKGROUND OF THE INVENTION

Protein conjugates are important reagents for a variety of important biomedical applications. Linking small molecules to proteins confers them with new properties. In particular, antibody conjugates have emerged as a critical reagent in a number of important clinical, diagnostic, and research uses such as antibody-drug conjugates, immunostains, and enzyme-linked immunosorbent assay (ELISA) and immunochromatography reagents.

Chemically linking small molecules to protein surfaces generate completely new functions for proteins and create novel reagents for biomedical research, diagnostics and therapeutics. These attachments occur by manipulating or creating reactive groups on the small molecules to covalently couple them to protein functional groups such as thiols, carboxylic acids, amines, and carbohydrates. The coupling reaction causes the small molecules to be stably attached to the protein surface.

Small molecule compounds are generally conjugated to proteins either by derivatizing the compound to a protein-reactive form, such as an isothiocyanate or maleimide derivative, or by using a bifunctional chemical crosslinking agent which attaches to both the small molecule and the protein, effectively linking them together.

Most synthetic organic chemistry reactions are performed in inert organic solvents to enhance chemical solubility and desolvate the reactants. Unfortunately, proteins are generally denatured and/or insoluble in organic solvents. Organic synthetic reactions involving proteins generally require an aqueous environment to maintain the function and solubility of the protein reactant. Therefore, protein conjugation reactions are performed in aqueous solutions. Over the years many tools, techniques and strategies have emerged to facilitate these important organic reactions in aqueous solutions.

For example, aprotic water-miscible organic solvents are sometimes added to aqueous solutions to decrease the overall solvent polarity to improve small molecule solubility while maintaining protein solubility. In doing so, coupling reactions usually achieve much greater efficiency compared to those performed in purely aqueous solvent systems. These tools and techniques have made it possible for these reactions to be routinely performed by investigators, clinicians and manufacturers with limited training and expertise in the field of synthetic organic chemistry.

Unfortunately, many important small molecules, such as fluorescent dyes and cytotoxic drugs, are poorly soluble in water, as indicated by log Pow values greater than 0, where log Pow is the log of the octanol-water partition coefficient. When added to aqueous solutions, these small molecules lose their desired reactivity as they precipitate from solution. To mitigate this problem limited amounts of water-miscible organic solvent (cosolvent), such as dimethyl sulfoxide (DMSO), are often added to the reaction medium to preserve small molecule solubility. Small molecule reactants are often dissolved to a high concentration in pure organic solvent. This reagent solution is then diluted into the aqueous protein solution. Organic co-solvent in the reaction mixture helps prevent both small molecule precipitation and non-specific binding to hydrophobic protein surfaces.

During the conjugation reaction, unwanted side reactions, such as hydrolysis, often occur in aqueous solvents. These side reactions, which compete with the desired coupling reaction, cause the small molecule reagents to appreciably degrade into unwanted side products. As the reaction proceeds, these side products accumulate in the reaction mixture. As a practical consequence, an excess of reactive small molecule is generally added to the mixture to drive the desired reaction to a higher yield. The resulting final reaction mixture therefore contains the desired protein conjugate as well as substantial amounts of unwanted low molecular weight side products and unincorporated small molecule reagents and/or crosslinkers.

These small molecule impurities can often nullify the performance and value of the protein conjugate. For example, residual uncoupled fluorescent dyes can increase the undesirable background signals in immunostaining experiments to unacceptable levels. To limit the presence of uncoupled small molecules in the product, new methods have been developed to synthesize the conjugate in the solid state. However, these methods use expensive stationary phases which also reduce the area of protein surface accessible to the small molecule reagent.

For such reasons, unwanted small molecule side products and starting reagents are generally removed from final reaction mixtures to produce useful, enriched protein conjugates. Several important methods have been developed to perform this process including dialysis, using semipermeable membranes, or gel filtration (desalting) chromatography, which uses swollen beads of crosslinked hydrophilic polymers.

These beads contain pores which allow penetration of small molecules but exclude proteins and other macromolecules. Although a variety of gel filtration beads with various fractionation ranges are commercially available, beads with a nominal protein fractionation range of 1000-6000 Daltons (Da) are generally regarded as the optimal beads for protein desalting. Such desalting beads swell in size by up to 400% or more when they are fully hydrated with water. Their use in organic solvents is very limited since such solvents prevent normal hydration and swelling of the particles which significantly affects their size exclusion properties.

These techniques also remove the organic cosolvent from the product. These methods are fairly effective separation tools but suffer significant disadvantages which limit process productivity. Excess small molecules often bind tightly to protein surfaces. The propensity of small molecules to bind to proteins can significantly hinder their ability to diffuse through the membrane pores during dialysis. This binding can dramatically increase the amount of time required to remove the small molecules from the mixture; in these cases, effective dialysis can sometimes take many days to perform. When the binding of the small molecule to the protein is through hydrophobic interactions, the addition of small amounts of organic solvents to the mixture can improve the speed of the dialysis process.

Dialysis also produces a large volume of liquid waste. When the reactants are hazardous, this waste becomes hazardous as well and must be disposed of as a hazardous material. The side products of antibody-cytotoxic drug conjugates in particular are often very toxic. Dialysis of antibody-drug conjugates can produce large volumes of very toxic liquid waste. Proper disposal of hazardous waste is generally expensive and requires considerable time and effort. Improper disposal of such waste can cause health hazards and undesirable environmental damage.

Removal of excess small molecules from reactions using gel filtration chromatography produces less solvent waste and less time to perform, but gel filtration columns are generally less effective at removing small molecules than dialysis. Also, gel filtration columns are very difficult to scale up without substantially reducing the efficiency of separation efficiency. It is generally recommended that the volume of sample loaded onto the column be no greater than 30% of the bed volume.

Even at these limits, substantial amounts of small molecule are still retained in the eluent. These relatively high levels of residual impurities (>1% of the initial concentration) greatly diminish the usefulness of the conjugates in many diagnostic and biomedical applications. In general, additional processing of gel filtration purified conjugates is required to produce useful reagents for high sensitivity applications.

Accordingly, it is highly desirable to have more scalable, higher efficiency systems and media to remove excess small molecules from biomacromolecules in protein conjugation or crosslinking reaction mixtures.

SUMMARY OF THE INVENTION

Embodiments of the invention provide provides systems and media to purify small molecule-protein conjugates from crude mixtures containing excess reactants and side products that eliminate the drawbacks of existing systems and media.

In one aspect, a separation medium is provided. The separation medium comprises gel filtration chromatography beads having a nominal protein fractional range of about 1000 Da to about 5000 Da and having an internal adsorbent matrix derived from a hydrophobicized scaffold, wherein the gel filtration chromatography beads remove small molecules that are less than 1500 Da and have log Pow values greater than about −0.5 from biomacromolecules in aqueous mixtures.

In another aspect, a device for removing small molecules less than 1500 Da from aqueous protein solutions is provided. The device has a first layer of medium and a second layer of medium arranged in a column for a flow of fluid through the column with the first layer of medium disposed upstream from the second layer of medium in relation to the direction of fluid flow through the column. The first layer of medium comprises gel filtration chromatography beads having a nominal protein fractional range of about 1000 Da to about 5000 Da and having an internal adsorbent matrix derived from a hydrophobicized scaffold. And the second layer of medium comprising a gel filtration chromatography medium.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

For a better understanding of the invention, its operating advantages and the specific objects attained by its uses, reference should be had to the accompanying drawings and descriptive matter in which there are illustrated embodiments of the invention.

BRIEF DESCRIPTION OF THE DRAWINGS

The following drawings illustrate by way of example and are included to provide further understanding of the invention for the purpose of illustrative discussion of the embodiments of the invention. No attempt is made to show structural details of the embodiments in more detail than is necessary for a fundamental understanding of the invention, the description taken with the drawings making apparent to those skilled in the art how the several forms of the invention may be embodied in practice. Identical reference numerals do not necessarily indicate an identical structure. Rather, the same reference numeral may be used to indicate a similar feature of a feature with similar functionality. In the drawings.

DETAILED DESCRIPTION OF THE INVENTION

In the following exemplary description, numerous specific details are explained to provide a more thorough understanding of embodiments of the invention. It will be apparent, however, that an artisan of ordinary skill that the present invention may be practiced without incorporating all aspects of the specific details described herein.

This disclosure, in embodiments, provides systems and media to purify small molecule-protein conjugates from crude mixtures containing excess reactants and side products. In embodiments, purified small molecule-protein conjugates can be produced, such as biotinylated proteins, antigens, dye-conjugated antibodies or antibody-drug conjugates.

In embodiments, to prepare these conjugates, a small molecule is chemically derivatized in order to directly link it to the protein or coupled to a crosslinking agent to enable its attachment to the protein. The protein and the small molecule reactants are combined in an aqueous environment to permit attachment of the small molecule to the protein without denaturing the protein.

Embodiments of the invention can be used to remove target hydrophobic or amphipathic small molecule contaminants (such as side products, unincorporated small molecule derivatives, and crosslinking agents) from the mixture after completion of the reaction.

Although embodiments of this disclosure enable facile production of purified protein and antibody conjugates, it is evident that an individual of ordinary skill in the art could apply the concepts disclosed herein to purify conjugates produced by the chemical attachment of small molecules to other types of water-soluble macromolecules including, but not limited to, nucleic acid duplexes, single-stranded DNA and RNA oligonucleotides, aptamers, dendrimers, and hydrogels.

The small molecule might be a fluorescent dye, vitamin, peptide, lipid or drug which is useful when chemically attached to a protein molecule. Embodiment of the invention are especially useful for removing uncoupled hydrophobic or amphipathic small molecules and undesired side products from aqueous reaction mixtures.

In embodiments, a column or cartridge containing a packed bed of modified porous, semi-permeable particles which exclude proteins and other biomacromolecules is provided. These particles comprise crosslinked hydrophilic polymers such as polysaccharides or polyacrylamide. The hydrophilic nature of these particles renders them well-suited as purification medium for samples in aqueous solutions. When immersed into aqueous solutions, these particles hydrate and swell to form hydrophilic porous beads. The hydration process causes the formation of pore-gated internal cavities accessible only to small molecules. The particle pore size is small enough to exclude proteins and other large biomolecules (molecular weight greater than 5000 Dalton (Da)) from diffusing into the particle. Large biomolecules flow through the exterior space surrounding the particle bed while solvent and other small molecules (less than 1500 Da) can enter porous channels at the particle surface and diffuse into the particle interior.

In embodiments, the particles contain an internal insoluble hydrophobicized adsorbent matrix which binds hydrophobic or amphipathic small molecules. The matrix resides within the interior of the particles which is accessible only to small molecules capable of passing through the pores. The matrix is constructed of a chemically-modified insoluble polymeric scaffold. The polymer contains attached aromatic or alipathic moieties which increase the hydrophobicity of the matrix surface to create a sorbent within the particle interior. As target hydrophobic or amphipathic small molecules in aqueous solutions diffuse throughout the internal region of the particles, they come into contact with and tightly bind the sorbent matrix.

Increasing the hydrophobicity of the adsorbent matrix improves its observed propensity and capacity to capture target hydrophobic molecules which penetrate the surface of the particle. The scaffold may be polyacrylamide or polyamide (or other polymers derived from water soluble monomers) assembled within the interior of the hydrated swollen particle. The initial polymeric scaffold structures are too hydrophilic to serve as an effective sorbent to bind hydrophobic target molecules. Subsequent hydrophobicization of the scaffold is required to increase its hydrophobicity to create a useful adsorbent surface. Hydrophobicized scaffolds contain attached aromatic or aliphatic moieties such as naphthyl, biphenyl, benzyl, octyl, and hexyl groups.

The binding properties of the sorbent can be varied by altering the chemical structure(s) of the hydrophobic moieties subsequently attached to the polymerized scaffold. The hydrophobized sorbent scaffold is accessible to small molecules, stably retained within the interior cavities and is not covalently attached to the particles. Particles containing the assembled matrix retain their ability to desalt proteins in aqueous solutions.

In an embodiment, the particles contain an internal matrix derived from methacrylamide or acrylamide. Water soluble monomers such as 2-aminoethylmethacrylamide or 3-aminopropylmethacrylamide are soaked into hydrated gel filtration chromatography desalting beads (having a nominal protein fractionation range of about 1000 to 5000 Da) and polymerized in situ to create a derivatizable internal scaffold. The derivatizable scaffold polymer or copolymer can also be produced using N-acryloyl-L-valine monomers. A variety of other water-soluble, chemically-derivatizable monomers, especially monomers producing polymers containing primary amine, secondary amine, or carboxylic acid groups such as 2-acetamidoacrylic acid or 2-aminoethyl methacrylate could also be useful to build the internal scaffold.

In another embodiment, a polyamide polymer or copolymer is used as the hydrophobicizable scaffold. When diacids, such as glutaric acid suberic acid, or adipic acid, are linked to monomers containing two primary amino groups and at least one secondary amino group, such as N,N'-Bis (3-aminopropyl)-1,3-propanediamine, N-(3-aminopropyl)-1,4-diaminobutane, or triethylenetetramine, using primary amine-specific crosslinking reagents such as N-(3-dimethylaminopropyl)-N'-ethylcarbodiimide (EDAC), the resulting polyamide copolymer contains reactive secondary amino groups which can then be used to chemically attach hydrophobicization reagents to the scaffold. Similar derivatizable copolymers could also be produced from copolymerizing diacids with monomers containing more than two primary amino groups.

Hydrophobicization of the polymeric scaffolds containing primary amino groups (such as polymers containing 3-aminopropylmethacrylamide) can be performed using alkylation, acylation or arylation reagents containing an amine-reactive substituent such as an isothiocyanate, sulfonyl chloride, anhydride, or succinimidyl ester substituents. and particularly useful amine reactive reagent for scaffold hydrophobicization. N-alpha-N-epsilon-Bis-benzyloxycarbonyl-L-lysine succinimidyl ester (Cbz-Lys(Cbz)-NHS) is a particularly useful arylation reagent to hydrophobicize internal polymers containing primary amines.

If the scaffold contains secondary amino groups (such as copolymers containing N,N'-Bis(3-aminopropyl)-1,3-propanediamine), the hydrophobicization cannot be performed using derivatization reagents specific for primary amino groups, such as succinimidyl esters. 9-fluorenylmethyl chloroformate is a particularly useful arylation reagent for polymers containing secondary amines. If the scaffold contains carboxylic acid groups (such as polymers containing N-acryloyl-L-valine), the hydrophobicization can be performed by crosslinking arylamines or alkylamines such as 1-naphthylmethylamine or octylamine, respectively, to the polymer using N-(3-dimethylaminopropyl)-N'-ethylcarbodiimide.

In all cases the hydrophobicization can be performed by directly attaching aryl, acyl or alkyl groups to the polymeric scaffold or by attaching these groups to a spacer group or branched amine such as 1,10 diaminodecane or trilysine containing reactive groups which is attached to the polymer in an intermediate step.

These particles are useful when they are packed into columns. When applied reaction mixtures containing protein conjugates and uncoupled small molecules flow through the column, the small molecules penetrate the internal cavities and become bound to the adsorbent scaffold within the particles, while the macromolecular conjugates can freely flow between the particles through the device. Once bound to the sorbent matrix, the small molecules are prevented from diffusing out of the particles. The binding interaction between the hydrophobic scaffold and the small molecule moiety is sufficiently strong to withstand the solubilizing effect of low concentrations of water-miscible organic solvents typically present in protein conjugation reaction mixtures (up to 10-20%). In doing so, solutions emerging from the device outlet contain greatly reduced levels of small molecule contaminants.

In embodiments, medium according to aspects of the invention can be made starting with gel filtration chromatography protein desalting beads (having a fractionation range of 1000-6000 Da). These beads are initially hydrated with an aqueous solution containing derivatizable water-soluble monomers. The volume of the hydration solution is less than 3.5 milliliters per gram of desalting beads. This solution contains the dissolved monomers used to build the internal scaffold. The concentration of monomer in the solution should be at least 1% (weight/volume).

During the hydration process, the monomers in the solution diffuse into the internal cavities. The hydration solution should contain at least 60% water to enable adequate hydration and swelling of the particles to enable access of the monomers into the interior of the particle. Therefore, the monomers must have appreciable water solubility (at least 15 milligrams per milliliter (mg/ml) in solutions containing at least 60% water). Examples of useful monomers to build polyacrylamide-based scaffolds include 3-aminopropylmethacrylamide, 2-aminoethylmethacrylamide, and N-acryloyl-valine. To make useful polyamide copolymer-based scaffolds, water-soluble monomers combinations such as N,N'-Bis(3-aminopropyl)-1,3-propanediamine with glutaric acid or N-(3-aminopropyl)-1,4-diaminobutane with suberic acid are useful. To promote precipitation of the scaffold, soluble diamines such as 1,6 diaminohexane, 1,8 diaminooctane, or 1,10 diaminodecane can be included in these mixtures.

Once internalized, the monomers are then polymerized within the hydrated interior of the particle to create an internal polymeric scaffold. Crosslinking or polymerizing reagents can be present in the hydration solution or can be added to the swollen particles after hydration. Examples of polymerization reagents include ammonium persulfate for polyacrylamide-based scaffolds and N-(3-dimethylaminopropyl)-N'-ethylcarbodiimide for polyamide-based scaffolds. The mixture is tumbled for room temperature for at least 10 minutes to promote even distribution of the reagents throughout the slurry. The polymerization reaction is allowed to proceed for at least 4 hours. The particles are then washed extensively with buffer solutions to remove unincorporated monomer and other reagents.

Next hydrophobic (aryl, acyl or alkyl) groups are chemically-attached to derivatizable functional groups on the polymeric scaffold to create a more hydrophobic adsorbent surface. The washed particles are equilibrated in buffered solutions containing at least 40% organic cosolvent such as dimethyl sulfoxide in order to maintain the solubility of the derivitization reagents used to hydrophobicize the scaffold. The hydrophobic reagents must possess the appropriate reactive group to modify the functional groups present on the scaffold. These reagents must also possess appreciable solubility (greater than 5 mg/ml) in solvents containing at least 40% water since significant water concentrations are generally required to maintain the accessible pore structure during the subsequent hydrophobization reaction. The reagents are dissolved in organic solvents such as DMSO and then diluted to into buffered water/cosolvent solutions. After dilution, the reagent is mixed with the equilibrated slurry. The reaction mixture is mixed by rotation or rocking for at least 60 minutes to allow thorough penetration and contact of the reactants with the interior scaffold. The particles are then thoroughly washed with solutions containing at least 40% organic cosolvent such as dimethyl sulfoxide to remove unwanted reactants and side products from the medium.

Scaffolds containing primary amine groups are hydrophobicized with appropriate amine-reactive aromatic groups of appreciable solubility in water-organic cosolvent mixtures. Examples of useful amine-reactive hydrophobicization reagents include 9-fluorenylmethyl chloroformate, biphenyl-4-sulfonyl chloride, 1-naphthyl isothiocyanate, fluorescein 5(6)-isothiocyanate, and the N-hydroxysuccinimidyl esters of N-Benzyloxycarbonyl-L-leucine (Cbz-Leu-NHS) and N-alpha-N-epsilon-Bis-benzyloxycarbonyl-L-lysine (Cbz-Lys(Cbz)-NHS). Reagents containing hydroxysuccinimidyl ester groups are not appropriate for derivatization of scaffolds containing secondary amine groups such as polyamides. However, it reasonable to one of ordinary skill that many other hydrophobic amine-reactive reagents would also be useful for production of the hydrophobic scaffold including aromatic acid chlorides, aromatic isothiocyanates, fluorophenyl esters, aldehydes, carboxylates and anhydrides, provided the reagents are appreciably soluble and stable in solutions containing at least 40% water. The propensity and capacity to bind hydrophobic and amphipathic small molecules is increased when more hydrophobic groups, such as N-alpha-N-epsilon-bis-benzyloxycarbonyl-L-lysine (Cbz-Lys(Cbz) or N-benzyloxycarbonyl-L-leucine-groups (Cbz-Leu), are attached to the polymer compared to less hydrophobic groups such as N-benzyloxycarbonyl-L-glutamine (Cbz-Gln). The polymeric scaffold sorbent is not covalently tethered to the bead structure; its large size and hydrophobic character prevent it from exiting the particle interior.

After assembly and hydrophobization of the internal scaffold, the particles are washed and fully swollen with buffer. The manufactured beads retain their ability to exclude proteins and maintain permeability to small molecules (less than 1500 Da) in aqueous solutions.

In an embodiment, a column containing the particles is provided. When aqueous conjugate reaction mixtures are applied to the particles, hydrophobic or amphipathic small molecules such as uncoupled dyes or drugs are able to diffuse into the interior space of the beads and bind to the interior adsorbent, while the biomacromolecular conjugates are excluded and do not enter the particle interior space. Aqueous conjugate solutions exiting the device therefore contain substantially less amounts of uncoupled small molecule impurities than present in the original mixture applied to the device. In another embodiment, the particles are a dry powder or suspension which is dispersed into aqueous samples to selectively remove undesirable small molecules from the sample.

Figure 2:
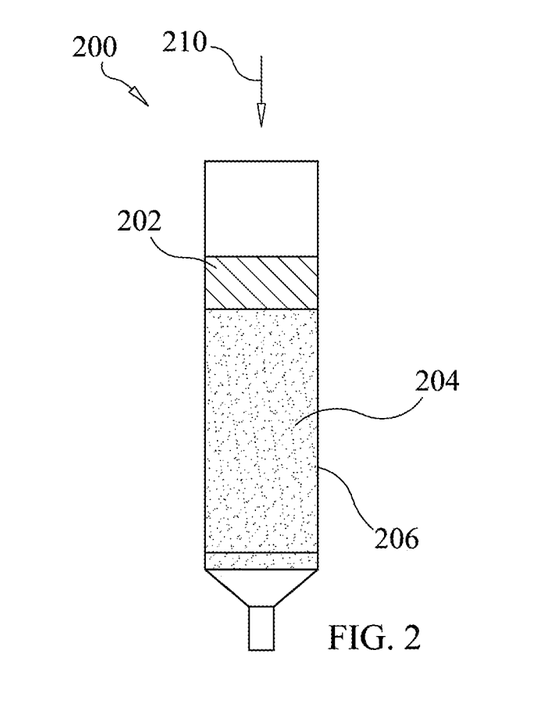
FIG. 2 diagrammatically shows a two-stage device in accordance with embodiments of the invention.

In other embodiments, the scaffold-containing particles are used in conjunction with unmodified desalting medium in a multi-layer configuration (See FIG. 2). This embodiment is particularly useful for purification of conjugates and other macromolecules from reaction mixtures containing a combination of unwanted hydrophilic and hydrophobic small molecules. The device contains an upper layer of particles containing an internal adsorptive scaffold and a lower layer of unmodified desalting medium. This device uses these layers sequentially to purify conjugates from mixtures. Samples exiting the modified medium immediately flow into the lower desalting layer. When reaction mixtures are applied to the device, they first enter the modified medium layer where excess hydrophobic and amphipathic small molecules adsorb to the internal scaffold while the macromolecules are permitted to pass through. After the sample exits the modified medium layer it enters the desalting layer. In this lower layer, removal of hydrophilic impurities and buffer exchange is performed using the normal desalting process.

Important hydrophilic impurities can include salts, water-miscible organic solvents, sugars, metal ions, and chelating agents. Therefore, the conjugate emerges from the device essentially free of organic solvents as well as hydrophobic/amphipathic and hydrophilic impurities. This device has two important advantages over existing gel filtration methods for purification of protein conjugates. Firstly, since the internal scaffold actively absorbs impurities, a substantially higher amount of impurity is removed from the mixture which produces products of higher purity. Secondly, it permits the higher volumes of sample to be loaded compared to conventional desalting columns. Toxic or hazardous small molecules are concentrated within the device, eliminating the production of large volumes of waste produced by dialysis- or diafiltration-based purification methods.

The adsorption of undesired small molecules to the internal sorbent scaffold within the porous particles provides rapid and highly efficient removal of small molecule impurities from protein samples compared to current dialysis and gel filtration methods. Consequently, the current invention is much faster than passive dialysis methods and is not constrained by the sample volume limitations intrinsic to gel filtration techniques.

The following discussion provides some specific examples in accordance with embodiments of the invention. It should be understood, however, that one of ordinary skill in the art would appreciate that other methods or processes could be implemented while staying within the scope of this disclosure. Accordingly, unless otherwise specified, the following examples should not be considered limiting.

Example 1

Production of a derivativable scaffold in the interior of desalting gel filtration beads by chemically-crosslinking internalized polyamine building blocks using glutaraldehyde.

Initially, 2.5 grams of dry Sephadex® G-25 medium was added to 7 mL of 0.12 M sodium phosphate buffer, 1.4 M NaCl, pH 6.8 and 0.05 mL of N,N'-Bis(3-Aminopropyl)-1, 3-propanediamine in a 50 mL tube. After allowing the medium to evenly hydrate and swell for 30 min at room temperature, a 0.2 mL solution of 50% acetone containing 12.5% glutaraldehyde was slowly added to the slurry. The mixture was tumbled in the tube for 15 min to facilitate more uniform distribution of the reagents within the scaffold. Next, 1 mL of 2.5% glutaraldehyde in 1× phosphate-buffered saline (PBS) buffer, pH 7.4 was added to the mixture. After tumbling the mixture for 15 min to distribute the reagents, the solution was incubated overnight at room temperature. The medium was then washed 4 times with 35 mL 1×PBS buffer, pH 7.4 to remove unincorporated reagents and cosolvent. The washed medium can be loaded into a column or cartridge to selectively remove hydrophilic or amphiphilic small molecules from aqueous reaction mixtures.

Example 2

Production of a derivatizable scaffold in the interior of partially hydrated desalting beads by chemically crosslinking polyamine building blocks within desalting gel Titration beads.

Initially, 2.5 grams of dry Sephadex® G-25 medium was added to 7 mL of 0.12 M sodium phosphate buffer, 1.4 M NaCl, pH 6.8 and 0.05 mL of N,N'-bis(3-aminopropyl)-1, 3-propanediamine in a 50 mL tube. After allowing the medium to evenly hydrate and swell for 30 min at room temperature, the mixture was tumbled in the tube for 15 min to facilitate more uniform distribution of the reagents within the scaffold. Next, 1.3 mL of 20 mg/ml bis(sulfosuccinimidyl) suberate in 100 mM sodium phosphate, 0.14 M sodium chloride, pH 7.4 was added to the mixture. After tumbling the mixture for 15 min to distribute the reagents, the solution was incubated overnight at room temperature. The medium was then washed 4 times with 35 mL PBS buffer, pH 7.4 to remove unincorporated reagents and cosolvent. The washed medium can be loaded into a column or cartridge to selectively remove hydrophilic or amphiphilic small molecules from aqueous reaction mixtures.

Example 3

Production of a derivatizable scaffold in the interior of gel filtration desalting beads using acrylamide monomers in water-cosolvent mixtures and then attaching hydrophobic groups to the scaffold to make it more hydrophobic.

Into a 50 ml plastic centrifuge tube, add 2 mL 0.25 M Na-HEPES (sodium N-(2-hydroxyethyl)piperazine-N'-ethane sulfonic acid), pH 8.5, 1 mL 40% acrylamide, 2 mL 1.5% bis-acrylamide, 1 mL 35% 3-aminopropylmethacrylamide hydrochloride (pH adjusted to a value between 7.5 and 8.5 using 10 M sodium hydroxide), and 4 mL acetone. Next, successively add 0.2 mL 4.5% potassium persulfate and 0.04 mL TEMED (N,N,N',N'-Tetramethylethylenediamine) and 3.3 grams Sephadex G-25 medium to the solution; mix gently by swirling for 15 seconds after each addition. Incubate the resulting thick slurry for 3 minutes and agitate by tumbling for 30 minutes. After allowing the mixture to incubate for an additional 30 minutes without agitation, further hydrate the mixture with 30 ml 50 mM Na-HEPES pH 8 and gently mix by inversion. Allow the medium to settle for 15 minutes and decant the liquid from the tube. Repeat the wash step with another 25 mL of 50 mM Na-HEPES pH 8. Wash the medium three more times with 25 mL 55% DMSO with 150 mM HEPES pH 8.5. Allow the medium to completely settle after the last wash and decant the liquid from the tube. Next add 20 mL of 50 mg/mL Cbz-L-glutamine N-hydroxysuccinimide ester (Cbz-Gln-NHS) in 50% DMSO to the tube and tumble the mixture for 60 minutes to thoroughly mix the reagents. Wash the derivatized medium (PAPMAG25-ZQ) three times with 25 mL 50% DMSO and then twice with 50 mM Na-HEPES pH 8.

Example 4

Removal of unbound fluorescent dye from protein molecules using a column of desalting gel filtration beads containing a hydrophobicized inner matrix.

Washed PAPMAG25-ZQ medium slurry was loaded into an empty, fritted solid phase extraction (SPE) cartridges to form a 7 mL packed bed. The packed columns were then equilibrated with 30 mL 1×PBS, pH 7.4 buffer before loading a 1 mL aliquot of a crude conjugation reaction mixture containing 5 mg/mL bovine serum albumin and 5 mg/mL Rhodamine B isothiocyanate in 0.2 M sodium carbonate buffer pH 9.4 containing 15% DMSO. Before loading onto the column, the mixture was centrifuged for 2 minutes at 4000 rpm to clarify the sample. After loading, 1×PBS, pH 7.4 buffer was slowly applied to the column to allow the conjugate to pass through the column. The dark-colored protein conjugate eluted from the column after 2-3 mL of buffer had been applied to the column. A colored band, comprised of incorporated Rhodamine B isothiocyanate and related side products, remained tightly bound to the top portion of the column.

Example 5

Production of a derivatizable scaffold in the interior of partially-hydrated desalting gel filtration beads using acrylamide monomers in water-cosolvent mixtures and then attaching hydrophobic groups to the scaffold to make it more hydrophobic.

In a 250 ml flask, combine 3 ml 1.5% bis-acrylamide, 3.3 ml 40% acrylamide, 4 ml 25% 3-aminopropylmethacrylamide HCl in 0.15 M sodium carbonate, 9 ml acetone and 1.5 ml distilled water. Mix gently by swirling for 15 seconds and add 0.6 ml potassium persulfate and 0.3 ml TEMED. Mix gently by swirling for 5 seconds and immediately add 10 g Sephadex® G-25. Mix by rocking for 45 minutes at room temperature. Wash the medium with 100 ml 50% DMSO, then with 100 ml 50% acetone, then with 125 ml distilled water and then with 125 ml 25 mM sodium phosphate (dibasic). Then wash the medium three times with 150 ml 100 mM sodium bicarbonate/60 mM sodium borate. Completely decant excess liquid from the medium and then add an equal volume of DMSO. Allow the flask to cool to room temperature. Add 30 ml 25 mg/ml N-alpha-N-epsilon-bis-benzyloxycarbonyl-L-lysine succinimidyl ester (Cbz-Lys (Cbz)-Nhs) in 50% DMSO to the flask. Rock for 45 minutes at room temperature. Decant liquid and wash this medium (PAPMAG25-ZKZ) twice with 200 mL solution of 100 mM sodium bicarbonate/60 mM sodium borate.

Example 6

Removal unbound biotin derivatives from protein molecules using a column containing desalting gel filtration beads containing a hydrophobicized inner matrix.

Initially, 7 ml washed PAPMAG25-ZKZ medium slurry was loaded into empty, fritted SPE cartridges to form 5 mL packed beds in each. The packed column was then washed and equilibrated with 1×PBS pH 7.4 before loading a 1 mL sample of a crude conjugation reaction mixture containing 5 mg bovine serum albumin-biotin conjugate with 0.5 mg biotin and 0.5 mg biotin-succinimidyl ester in 1×PBS containing 5% DMSO. After loading, 8 ml 1×PBS pH 7.4 buffer was slowly applied to the column and eight 1 ml fractions were collected to measure the biotin content in each by competitive ELISA assay and the protein content by colorimetric Coomassie BB G-250 assay. The performance was directly (side-by-side) compared to a column packed with 5 ml of unmodified Sephadex® G-25 equilibrated with 1×PBS. The BSA protein conjugate eluted from the column after 2-3 mL of buffer had been applied to the column as expected, while the fractions contained significantly lower biotin compared to an unmodified G-25 Sephadex column (packed volume of 5 ml).

Example 7

Removal of unbound dye from a protein sample using a column containing desalting gel filtration beads containing a hydrophobicized inner matrix.

Initially, 4 mL washed PAPMAG25-ZQ medium (50% slurry) was gently loaded into fritted column containing 5 mL of packed Sephadex® G-25 medium. The medium was allowed to settle and the column was washed and equilibrated with 30 mL 1×PBS pH 7.4 buffer before loading a 1 mL aliquot of reaction product containing 5 mg BSA and 5 mg Rhodamine B isothiocyanate in 0.2 M sodium carbonate buffer pH 9.2 containing 15% DMSO. Before loading, the sample was centrifuged briefly at 4000 rpm to clarify the solution. After loading, 4 mL 1×PBS pH 7.4 buffer was applied to the column to allow the protein to flow through the device. A substantial amount of the Rhodamine B dye was bound to the top layer of the column.

Example 8

Production of desalting gel filtration beads containing a derivatizable internal polyamide scaffold.

In a 50 ml plastic tube, combine 2 ml 0.32 M Pentaethylenehexamine HCl, pH 7, 1.2 ml 1 M glutaric acid pH 5.5, 4 ml 0.16 M 1,10 diaminodecane HCl pH 7, 2.4 ml 1 M 2-(N-morpholino)ethanesulfonic acid (MES) pH 4.8. and 4.2 ml 0.6 M EDAC. Mix for 5 seconds and immediately add 4 grams G-25 Sephadex. Mix by tumbling for 20 min and then incubate for 16 hours at room temperature. Wash the medium (PHADADG1G25) three times with 30 ml 100 mM sodium bicarbonate/60 mM sodium borate.

Example 9

Hydrophobicization of the internal polyamide scaffold within desalting gel filtration beads.

In a 50 ml plastic tube, wash 5 ml PHADADG1G25 medium once with 40 ml 0.15 M sodium carbonate and then resuspend the pellet in 19 ml 0.15 M sodium carbonate. Add 20 ml acetonitrile then add 4 ml 50 mg/ml 9-fluorenylmethyl chloroformate in acetonitrile. Mix by rocking the tube for 60 minutes at room temperature. Decant the liquid supernatant. Wash the medium (PHADADG1G25-FM) twice with 40 ml 80% methanol and then twice with 40 ml 1×PBS.

Example 10

Hydrophobicization of the internal polyamide scaffold within desalting gel filtration beads.

In a 50 ml plastic tube, wash 5 ml PHADADG1G25 medium once with 40 ml 0.2 M sodium bicarbonate buffer pH 9.2. Add 3 ml acetonitrile to the pellet. and then resuspend the pellet in 19 ml 0.2 M sodium bicarbonate buffer pH 9.2. Dilute 2 ml 40 mg/ml biphenyl-4-sulfonyl chloride in acetonitrile into 22 ml 0.1 M sodium bicarbonate buffer pH 9.2 in 50% acetonitrile and then add this solution to the medium. Mix by rocking the tube for 60 minutes at room temperature. Decant the liquid supernatant. Wash the medium (PHADADG1G25-BP) twice with 40 ml 50% ethanol and then twice with 40 ml 1×PBS.

Example 11

Production of porous hydrophilic beads containing an internal polymeric matrix containing carboxyl groups.

Initially, combine 2.2 ml of 15% N-acryloyl-L-valine in 50% dimethyl sulfoxide, 0.5 ml 1.5% bis-acrylamide, 0.4 ml dimethyl sulfoxide, 1 ml distilled water, and 1.2 ml 0.67 M HEPES-NaOH pH 8 in a plastic 50 ml conical tube. Mix gently by swirling for 10 seconds. Next sequentially add 0.4 ml of 5% potassium persulfate and 0.15 ml TEMED. Mix gently by swirling for 10 seconds and immediately add 3 grams of Sephadex G-25. Mix thoroughly by tapping and tumbling for 20 minutes to distribute the acrylamide solution throughout the medium. Allow the mixture to polymerize for 3 hours then suspend the medium in 35 ml 25 mM 0.67 M HEPES-NaOH pH 7 to promote complete hydration of the particles. After 60 minutes, decant the supernatant and wash the pellet twice with 35 ml of distilled water and then twice with 30 ml of matrix twice with 30 ml 0.1 M HEPES-NaOH pH 7 to yield 14 ml of hydrated ZNJG-25COOH1 medium.

Example 12

Hydrophobicization of carboxyl groups residing in an internal polymeric matrix within porous hydrophilic beads.

Dissolve 0.4 grams of EDAC and 0.5 g of N-hydroxysulfosuccinimide in 10 ml of 50 mM HEPES-NaOH pH 6.5/50% acetone. Add this solution to 14 ml of ZNJG-25COOH1 medium in a 50 ml plastic conical tube. Mix briefly by inversion and add 4 ml of 10% 1,10 diaminodecane. Mix by rocking for 2 hours and then wash the medium four times with phosphate buffered saline pH 7.4. Resuspend the medium in 26 ml 0.3 M HEPES-NaOH pH 8.5, transfer the slurry to a 250 ml glass Erlenmeyer flask containing 60 ml of acetone. Swirl the flask for 5 seconds to mix then allow the medium to settle and decant 60 ml of the liquid. Dissolve 1 gram of Cbz-Lys(Cbz)-NHS in 50 ml acetone in a 125 ml glass flask. While swirling, slowly dilute with 10 ml distilled water and then with 20 ml 0.15 M HEPES-NaOH pH 8. Gently swirl to mix and then add this solution to the flask containing the medium. Gently rock for 3 hours at room temperature. Wash 10 ml medium (ZNJG-25CO-ZKZ) three times with 50% acetone and then three times with phosphate buffered saline.

Example 13

Removal of a cytotoxic drug from an antibody solution.

Load 1.2 ml of a mixture containing 2 mg doxorubicin and 2.5 mg bovine IgG onto a 5 ml column of ZNJG-25CO-ZKZ equilibrated with phosphate buffered saline. Apply phosphate buffered saline to the column and collect 1.2 ml fractions eluting from the column. Under these conditions, the antibody passes through the column in the void volume while the doxorubicin drug remains bound to the beads. Analysis of the fractions indicates that, as expected, the majority of the antibody is contained in the first two fractions (FIG. 3) while significant amounts of doxorubicin are only found in later fractions. In studies performed in parallel using unmodified Sephadex® G-25 medium, much higher concentrations of doxorubicin are found in the protein-containing fractions 2 and 3 (30-fold and 40-fold higher than observed in the corresponding ZNJG-25CO-ZKZ fractions, respectively).

Figure 1:
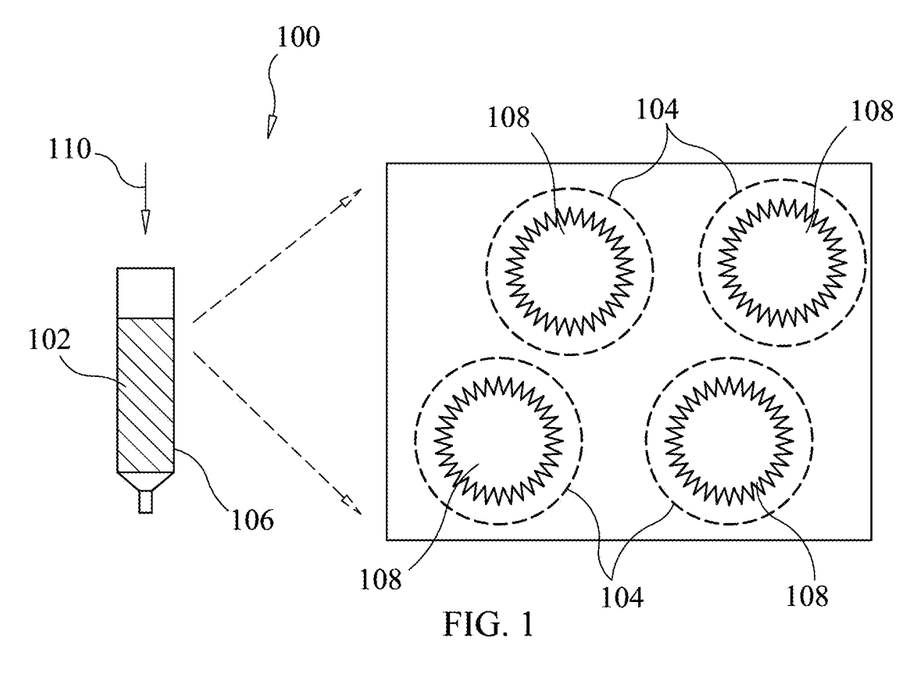
FIG. 1 diagrammatically shows a single-stage device in accordance with embodiments of the invention.

Turning now to the drawings, in FIG. 1 there is diagrammatically shown a device 100 in accordance with embodiments of the invention. Device 100 is configured for the selective remove of small molecules from aqueous solutions containing proteins or other macromolecules. The device 100 includes a packed bed 102 of porous hydrophilic particles 104 constructed in accordance with the principals of the present invention. The particles 104 are arranged in a column, for example in cartridge 106. The particles 102 have an inner absorbent matrix 108 derived from a hydrophobicized scaffold. When an aqueous solution 110 containing small molecules and macromolecules flows through the packed bed, the small molecules enter the particles 104 and diffuse into the inner space where they adsorb to the matrix 108. The macromolecules are unable to pass through the pores, so they flow unencumbered through the exterior, excluded space.

In FIG. 2 there is diagrammatically shown a device 200 in accordance with embodiments of the invention. Device 200 is configured for the selective removal of small molecules from aqueous solutions containing proteins or other macromolecules. Device 200 is a two-stage device and includes a first stage of a first layer of medium 202 and a second stage of a second layer of medium 204. The first and second layers of medium 202 and 204 are serially arranged with the first layer disposed upstream from the second layer in relation to a direction of flow through the layers. As representatively shown, the layers are arranged in a column, for example in a cartridge 206.

The first layer of medium 202 contains a packed bed of porous hydrophilic particles containing an internal adsorbent matrix constructed in accordance with the principles of the present invention. The second layer of medium 202 contains a bed of desalting or gel filtration medium. As fluid 206 flows through the device, it passes first through the first layer of medium 202 which causes selective removal of hydrophobic or amphipathic small molecules. As fluid exits this stage, it then passes through the second layer of medium 204 which permits further buffer exchange.

Figure 3:
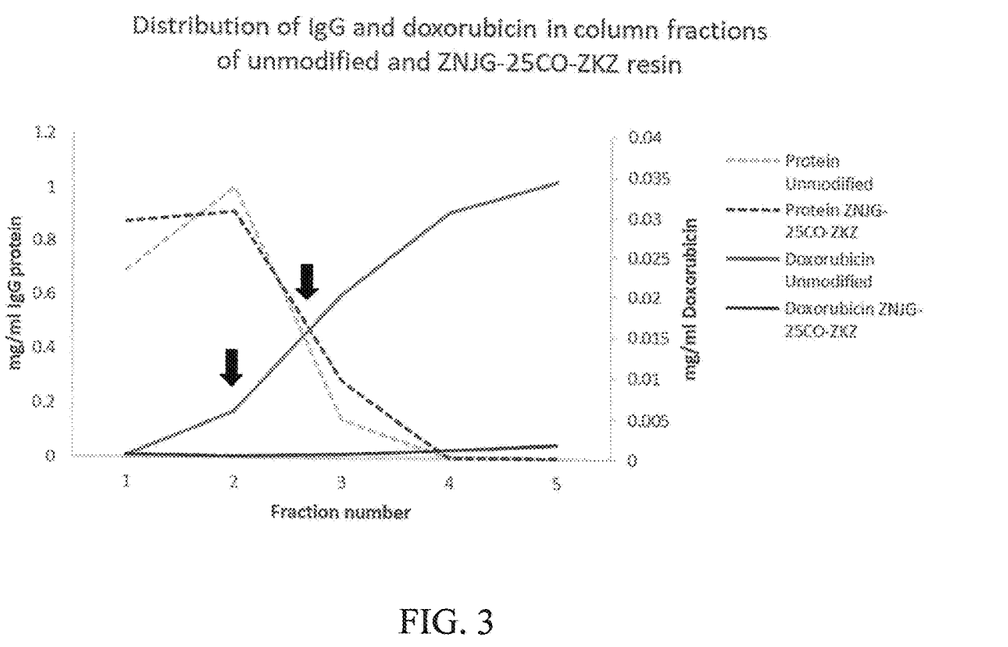
FIG. 3 is a chart demonstrating removal of unbound doxorubicin, a cytotoxic drug, from immunoglobulin (IgG) protein using embodiments in accordance with the invention.

In FIG. 3 there is shown chart demonstrating removal of unbound doxorubicin, a cytotoxic drug, from immunoglobulin (IgG) protein using embodiments in accordance with the invention. The chart shows the results of the following process: A 1.2 ml mixture of bovine immunoglobulin and doxorubicin are applied to the top of the 5 ml column containing the modified medium (ZNJG-25CO-ZKZ). PBS buffer is applied to the column and then one ml fractions are sequential collected and analyzed for presence of protein and doxorubicin. As expected, the protein is observed in the first three fractions. Very little doxorubicin is observed in the protein containing fractions. This is not observed when an identical sample is applied to a 5 ml column containing unmodified Sephadex® G-25 desalting medium—significant doxorubicin is observed in the protein two of the three protein-containing fractions (indicated by the arrowheads).

While the invention herein disclosed has been described by means of specific embodiments and applications thereof, numerous modifications and variations could be made thereto by those skilled in the art without departing from the scope of the invention set forth in the following claims.

What is claimed is:

1. A separation medium comprising:
gel filtration chromatography beads having a nominal protein fractional range of about 1000 Da to about 5000 Da and having an internal hydrophobicized adsorbent matrix having attached aromatic or aliphatic moieties and that is derived from a hydrophilic polymeric scaffold that has been hydrophobicized, wherein the gel filtration chromatography beads remove small molecules that are less than 1500 Da and have log P values greater than about −0.5 from biomacromolecules in aqueous mixtures.

2. The invention of claim 1, wherein the gel filtration chromatography beads are comprised of crosslinked polysaccharide.

3. The invention of claim 1, wherein the gel filtration chromatography beads are comprised of polyacrylamide.

4. The invention of claim 1, wherein the biomacromolecules include a protein.

5. The invention of claim 1, wherein the biomacromolecules include an oligonucleotide.

6. The invention of claim 1, wherein the biomacromolecules includes a nucleic acid duplex.

7. The invention of claim 1, wherein the biomacromolecules include a hydrogel.

8. The invention of claim 1, wherein the biomacromolecules include an antibody-drug conjugate.

9. The invention of claim 1, wherein the scaffold is a polyacrylamide.

10. The invention of claim 1, wherein the scaffold is a polyamide.

11. The invention of claim 1, wherein the internal adsorbent matrix contains attached phenyl groups.

12. The invention of claim 1, wherein the internal adsorbent matrix contains attached biphenyl groups.

13. The invention of claim 1, wherein the internal adsorbent matrix contains attached naphthyl groups.

14. The invention of claim 1, wherein the internal adsorbent matrix contains attached benzyl groups.

15. The invention of claim 1, wherein the internal adsorbent matrix contains attached phenyl groups.

16. The invention of claim 1, wherein the internal adsorbent matrix contains attached 9-fluorenylmethyl groups.

17. A separation medium comprising:
  gel filtration chromatography beads having a nominal protein fractional range of about 1000 Da to about 5000 Da and having an internal hydrophobicized adsorbent matrix that is derived from a hydrophilic polymeric scaffold that has been hydrophobicized, wherein the gel filtration chromatography beads remove small molecules that are less than 1500 Da and have log P values greater than about −0.5 from biomacromolecules in aqueous mixtures; and
  wherein the internal adsorbent matrix contains attached N-alpha-N-epsilon-bis-benzyloxycarbonyl-L-lysine groups.

18. The invention of claim 1, wherein the internal adsorbent matrix contains attached N-benzyloxycarbonyl-L-leucine groups.

19. The invention of claim 1, wherein the internal adsorbent matrix contains attached hexyl groups.

20. The invention of claim 1, wherein the internal adsorbent matrix contains attached octyl groups.

21. A device for removing small molecules less than 1500 Da from aqueous protein solutions comprising:
  a first layer of medium and a second layer of medium arranged in a column for a flow of fluid through the column with the first layer of medium disposed upstream from the second layer of medium in relation to the direction of fluid flow through the column;
  the first layer of medium comprising gel filtration chromatography beads having a nominal protein fractional range of about 1000 Da to about 5000 Da and having an internal hydrophobicized adsorbent matrix having attached aromatic or aliphatic moieties that is derived from hydrophilic polymeric scaffold that has been hydrophobicized; and
  the second layer of medium comprising a gel filtration chromatography medium;
  wherein the gel filtration chromatography beads remove small molecules that are less than 1500 Da and have log P values greater than about −0.5 from biomacromolecules in aqueous mixtures.

\* \* \* \* \*